United States Patent [19]
Barbier et al.

[11] Patent Number: 5,919,986
[45] Date of Patent: Jul. 6, 1999

[54] D-HOMO VITAMIN $D_3$ DERIVATIVES

[75] Inventors: Pierre Barbier, Rixheim, France; Franz Bauer, Reinach; Peter Mohr, Basel, both of Switzerland; Marc Muller, Saint-Louis, France; Wolfgang Pirson, Weil am Rhein, Germany

[73] Assignee: Hoffmann-la Roche Inc., Nutley, N.J.

[21] Appl. No.: 09/170,453

[22] Filed: Oct. 13, 1998

[30] Foreign Application Priority Data

Oct. 17, 1997 [EP] European Pat. Off. .............. 97118036

[51] Int. Cl.[6] .......................... C07C 49/115; C07C 35/08
[52] U.S. Cl. ......................... 568/376; 568/377; 568/822; 568/823; 568/828; 568/832; 568/833
[58] Field of Search ................... 568/822, 823, 568/828, 832, 833, 376, 377

[56] References Cited

U.S. PATENT DOCUMENTS

| | | |
|---|---|---|
| 4,804,502 | 2/1989 | Baggiolini et al. . |
| 5,384,314 | 1/1995 | Uskokovic et al. . |
| 5,488,183 | 1/1996 | DeLucia et al. .......... 568/828 |

FOREIGN PATENT DOCUMENTS

| | | |
|---|---|---|
| 0 580 968 | 2/1994 | European Pat. Off. . |
| 0 771 789 | 5/1997 | European Pat. Off. . |
| WO 95/01960 | 1/1995 | WIPO . |
| WO 97/19058 | 5/1997 | WIPO . |

OTHER PUBLICATIONS

Schwartz, G. et al., Urology, vol. 46, No. 3, 1995, pp. 365–369.
Wali, R.K., et al., Cancer Research vol. 55, No. 14, Jul. 15, 1995, pp. 3050–3054.
Tetrahedron Lett. 1996, vol. 37 pp. 9361–9364.
Tetrahedron Lett. 1992: vol. 33, pp. 2455–2458.
Tetrahedron Lett. 1991: vol. 32, pp. 7663–7666.
Tetrahedron Lett. 1996: vol. 37, pp. 5589–5592.
Tetrahedron Lett. 1992: vol. 33, pp. 4361–4364.
CA:126:104299 by Yong–Jun Chen abs of "Synthesis of new vitamin D3 analogs with a decalin–type CD–ring", Tetrahedron letts, 37(52), pp. 9361–9364, 1996.

Primary Examiner—Gary Geist
Assistant Examiner—Jean F Vollano
Attorney, Agent, or Firm—George W. Johnston; Patricia S. Rocha-Tramaloni; Robert A. Silverman

[57] ABSTRACT

Compounds of formula I:

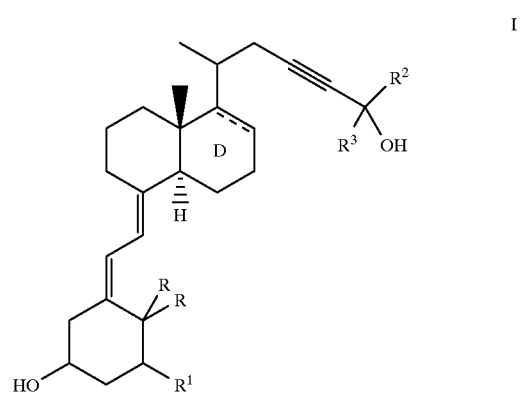

wherein the dotted carbon-carbon bond in the D-ring is C—C or C=C;
C(R,R) is $CH_2$ or $C=CH_2$,
$R^1$ is H, F or OH,
$R^2$ and $R^3$ are each independently $C_{1-4}$-alkyl or $CF_3$, or together with the carbon to which they are bound form $C_{3-6}$-cycloalkyl.

are useful in the treatment of vitamin D dependent disorders, such as psoriasis, leukemia; acne and seborrhoic dermatitis; osteoporosis hyperparathyroidism accompanying renal failure; and multiple sclerosis.

35 Claims, No Drawings

D-HOMO VITAMIN D₃ DERIVATIVES

BACKGROUND OF THE INVENTION

The term "vitamin D dependent disorders" refers to disorders which can be treated or prevented by the administration of compounds having vitamin D activity, such as vitamin $D_3$ or derivatives, in particular hydroxylated derivatives thereof, e.g. calcitriol or calcipotriol. Examples of such disorders are hyperproliferative skin diseases such as psoriasis, basal cell carcinomas, disorders of keratinization and keratosis; neoplastic diseases such as leukemia; disorders of the sebaceous glands such as acne and seborrhoic dermatitis; osteoporosis; hyperparathyroidism accompanying renal failure; and diseases which require modulation of the immune system, such as multiple sclerosis, transplant rejection and graft vs. host disease.

However, vitamin D activity is often coupled with an undesirable level of toxicity. It is important to obtain compounds that have vitamin D activity sufficient to combat vitamin D related disorders, which have as low as possible toxicity compatible with the activity.

SUMMARY OF THE INVENTION

The invention relates to novel polyunsaturated D-homo-9,10-secocholesta-23-yne-3,25-diol derivatives of formula I:

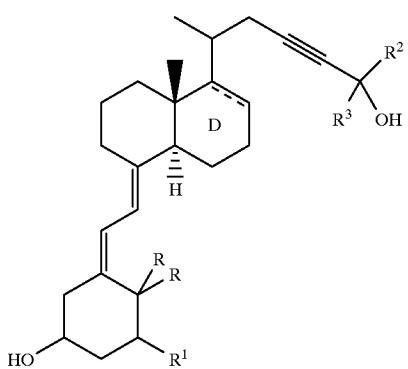

wherein the dotted C—C bond in the D-ring is optional,
C(R,R) is $CH_2$ or $C=CH_2$,
$R^1$ is H, F or OH,
$R^2$ and $R^3$ are each independently $C_{1-4}$-alkyl or $CF_3$, or
$C(R^2,R^3)$ is $C_{3-6}$-cycloalkyl.

The present invention furthermore relates to a process for the preparation of the compound of formula I, pharmaceutical compositions containing the compound of formula I, and the use of the compound of formula I for the treatment of vitamin D dependent disorders and for the manufacture of pharmaceutical compositions for the treatment of vitamin D dependent disorders.

The compounds of this invention have vitamin D activity combined with low toxicity that makes them particularly suitable for treatment of vitamin D related disorders, especially those relating to hyperproliferative skin disorders such as psoriasis, basal cell carcinoma, keratinization, and keratosis.

DETAILED DESCRIPTION OF THE INVENTION

This invention is directed to compounds of formula I:

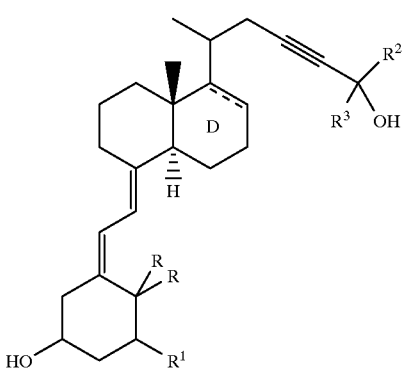

wherein the dotted carbon-carbon bond in the D-ring is C—C or C=C;
C(R,R) is $CH_2$ or $C=CH_2$,
$R^1$ is H, F or OH,
$R^2$ and $R^3$ are each independently $C_{1-4}$-alkyl or $CF_3$, or together with the carbon to which they are bound form $C_{3-6}$-cycloalkyl.

In preferred compounds of formula I, $R^2$ and $R^3$ are $CF_3$. In others, $R^2$ and $R^3$ are $C_{1-4}$-alkyl, preferably straight-chain alkyl such as propyl, ethyl, and methyl especially methyl or ethyl. In other preferred compounds, $R^2$ and $R^3$ together with the carbon to which they are bound form $C_{3-6}$-cycloalkyl, especially cyclobutyl, cyclopentyl or cyclohexyl, and preferably cyclopentyl or cyclohexyl.

Compounds where $R^2$ and $R^3$ are $CF_3$ include
(5Z,7E)-(1S,3S)-26,26,26,27,27,27-hexafluoro-D-homo-9,10-seco-cholesta-5,7,10(19),17-tetraen-23-yne-1,3,25-triol,
(7E)-(1R,3R)-26,26,26,27,27,27-hexafluoro-D-homo-9,10-secocholesta-5,7,17-trien-23-yne-1,3,25-triol.

Compounds where $R^2$ and $R^3$ are $C_{1-4}$-alkyl include
(5Z,7E)-(1S,3R)-1,26,26,26,27,27,27-heptafluoro-D-homo-9,10-secocholesta-5,7,10(19),17-tetraen-23-yne-3,25-diol,
(5Z,7E)-(3S)-D-homo-9,10-secocholesta-5,7,10(19),17-tetraen-23-yne-3,25-diol,
(7E)-(1R,3R,20S)-D-homo-19-nor-9,10-secocholesta-5,7,17-trien-23-yne-1,3,25-triol,
(5Z,7E)-(3S,20S)-D-homo-9,10-secocholesta-5,7,10(19),17-tetraen-23-yne-3,25-diol,
(7E)-(1R,3R)-17a,26a,27a-trihomo-9,10-secocholesta-5,7,17-trien-23-yne-1,3,25-triol,
(5Z,7E)-(1S,3R)-17a,26a,27a-trihomo-9,10-secocholesta-5,7,10(19),17-tetraen-23-yne-1,3,25-triol,
(5Z,7E)-(3S)-17a,26a,27a-trihomo-9,10-secocholesta-5,7,10(19),17-tetraen-23-yne-3,25-diol,
(5Z,7E)-(1S,3S)-D-homo-9,10-secocholesta-5,7,10(19),17-tetraen-23-yne-3,25-diol,
(5Z,7E)-(1S,3R)-1-fluoro-D-homo-9,10-secocholesta-5,7,10(19),17-tetraen-23-yne-3,25-diol,
(7E)-(1R,3R)-D-homo-19-nor-9,10-secocholesta-5,7-dien-23-yne-1,3,25-triol,
(5Z,7E)-(1R,3R)-D-homo-9,10-secocholesta-5,7,10(19)-trien-23-yne-1,3,25-triol,
(5Z,7E)-(1S,3S)-D-homo-9,10-secocholesta-5,7,10(19)-trien-23-yne-1,3,25-triol,
(5Z,7E)-(1S,3R)-D-homo-9,10-secocholesta-5,7,10(19)-trien-23-yne-1,3,25-triol, (5Z,7E)-(3S)-D-homo-9,10-seco-cholesta-5,7,10(19)-trien-23-yne-3,25-diol.

Compounds where $R^2$ and $R^3$ together with the carbon to which they are bound form $C_{3-6}$-cycloalkyl include (5Z,7E)-(3S)-24-(1-hydroxycyclopentyl)-D-homo-9,10-seco-chola-5,7,10(19),17-tetraen-23-yne-3-ol (7E)-(1R,3R)-24-(1-hydroxy-cyclohexyl)-D-homo-9,10-secochola-5,7,17-trien-23-yne-1,3-diol (5Z,7E)-(1S,3R)-24-(1-hydroxy-cyclopentyl)-D-homo-9,10-secochola-5,7,10(19),17-tetraen-23-yne-1,3-diol (7E)-(1R,3R)-24-(1-hydroxy-cyclopentyl)-D-homo-9,10-secochola-5,7,17-trien-23-yne-1,3-diol (5Z,7E)-(1S,3R)-24-(1-hydroxy-cyclohexyl)-D-homo-9,10-secochola-5,7,10(19),17-tetraen-23-yne-1,3-diol, (5Z,7E)-(3S)-24-(1-hydroxy-cyclohexyl)-D-homo-9,10-secochola-5,7,10(19),17-tetraen-23-yne-3-ol.

Compounds of formula I where $R^1$ is OH and the dotted carbon-carbon bond on the D ring is C=C are preferred. In particular such compounds are preferred where $R^2$ and $R^3$ are $C_{1-4}$-alkyl or $R^2$ and $R^3$ are $CF_3$ or $R^2$ and $R^3$ together with the carbon to which they are bound form $C_{3-6}$-cycloalkyl. In compounds where $R^2$ and $R^3$ are $C_{1-4}$ alkyl, it is additionally preferred that $R^2$ and $R^3$ are $CH_3$.

Examples of the latter compounds include (5Z,7E)-(1S,3R)-D-homo-9,10-secocholesta-5,7,10(19),17-tetraen-23-yne-1,3,25-triol, (7E)-(1R,3R)-D-homo-19-nor-9,10-secocholesta-5,7,17-trien-23-yne-1,3,25-triol, (5Z,7E)-(1S,3R,20S)-D-homo-9,10-secocholesta-5,7,10(19),17-tetraen-23-yne-1,3,25-triol.

Also part of this invention is a compound of formula II

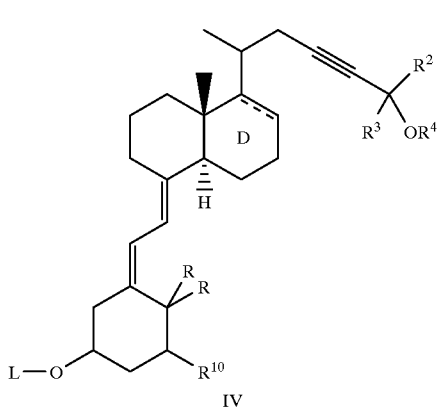

II wherein the dotted bond, R, $R^2$ and $R^3$ are as in claim 1, $R^4$ is H or L', and $R^{10}$ is H, F or O-L, wherein L and L' are tert-butyl-dimethylsilyl, tert-butyl-diphenylsilyl or trimethylsilyl.

Another compound of this invention is a compound of formula IV

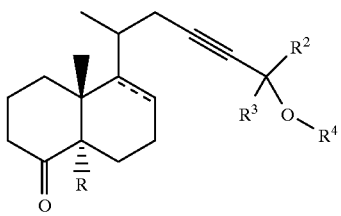

IV wherein the dotted bond, R, $R^2$ and $R^3$ are as in claim 1, $R^4$ is H or L', and $R^{10}$ is H, F or O-L, wherein L and L' are tert-butyl-dimethylsilyl, tert-butyl-diphenylsilyl or trimethylsilyl.

The invention is also directed to a process for the manufacture of a compound of formula I which comprises cleaving the protecting groups in a compound of formula

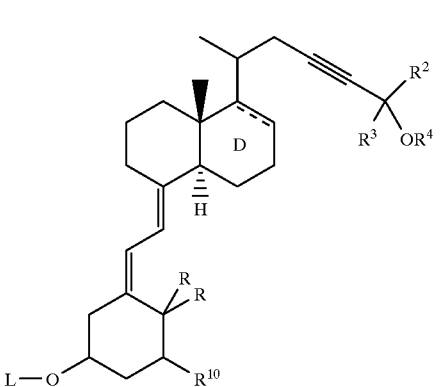

II wherein the dotted bond, R, $R^2$ and $R^3$ are as in claim 1, $R^4$ is H or L', and $R^{10}$ is H, F or O-L, wherein L and L' are tert-butyl-dimethylsilyl, tert-butyl-diphenylsilyl or trimethylsilyl.

The compounds of formula I can be obtained by cleavage of any silyl-protecting group L and L' contained in a compound of formula II

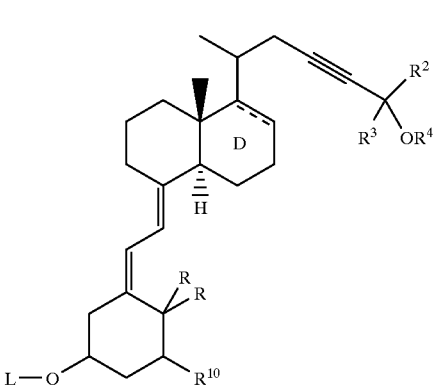

II wherein $R^{10}$ is H, F or O-L, and $R^4$ is H or L', in which L and L' are e.g. tert-butyl-dimethylsilyl (TBDMS), tert-butyl-diphenylsilyl (TBDPS) or trimethylsilyl (TMS).

The intermediates of formula II and those of formulae IV, V and VI are novel and as such are a further object of the present invention.

The cleavage of silyl-protecting groups in the compounds II can be effected by tetrabutylammonium fluoride (TBAF) in a solvent such as THF at a temperature up to 60° C.

The compounds of formula II are obtained by coupling a phosphine oxide of formula III

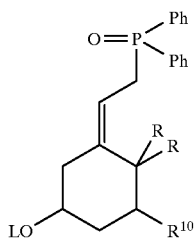

III with a ketone of formula IV

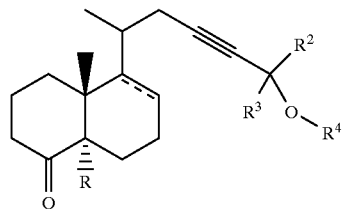

IV

The coupling can be effected by reacting a solution of the phosphine oxide in THF with n- or sec-butyl lithium and then with a ketone IV at −78° C.

The ketones IV can be obtained by oxidation of the corresponding diols of formula V

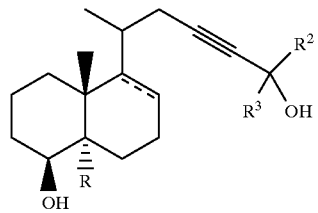

V if desired followed by silylation of the obtained hydroxy ketones of formula

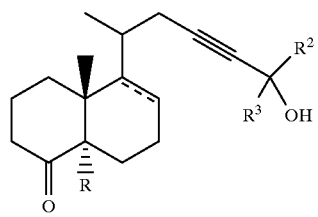

VI

The oxidation can be effected in DMF or in $CH_2Cl_2$ with pyridinium dichromate (PDC), or with N-methylmorpholine N-oxide and catalytic amounts of tetrapropylammonium perrhutenate, in the presence of molecular sieve.

The silylation of VI can be effected in THF or in $CH_2Cl_2$ e.g. with TMS-imidazole, or with TMS-chloride in the presence of triethylamine and catalytic amounts of 4-dimethylamino-pyridine (DMAP).

The diols V can be obtained by deprotecting a compound of formula VII

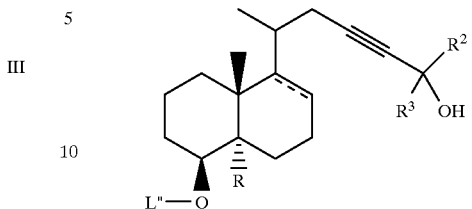

VII wherein L" is a silyl-protecting group, preferably TBDMS.

The deprotection of VII to the diol V can be effected with TBAF in THF.

The compounds of formula VII can be obtained by reacting a dibromide of formula

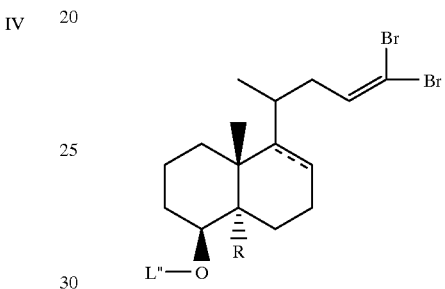

VIII with an organolithium compound, such as butyllithium, followed by the addition of a ketone of formula $O=C(R^2, R^3)$.

The dibromides VIII are obtained from aldehydes of formula

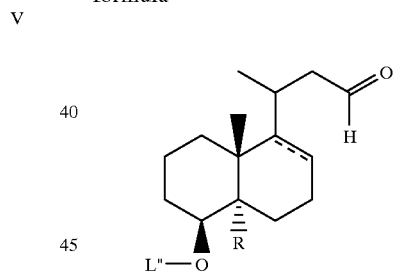

IX by reaction with tetrabromomethane in dichloromethane in the presence of triphenylphosphine at about −20° C.

The aldehydes IX can be obtained from alcohols of formula X

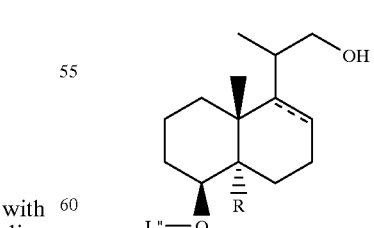

X by reaction with tosyl chloride in the presence of dimethylamino-pyridine in dichloromethane, then reacting the obtained tosylate with NaCN in DMSO at 90° C., and reacting the resulting cyanide with diisobutylaluminum hydride (DIBAH) in dichloromethane at −10° C.

In a variant, which is preferred when the aldehyde IX is unsaturated, the alcohol X is in a first step converted to the corresponding aldehyde, e.g. with Swern reagent. This aldehyde of formula XI

XI

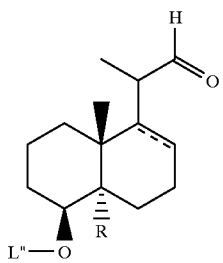

is in a second step reacted at −78° C. with an ylide solution, itself obtained by reaction of (methoxymethyl) triphenylphosphonium chloride in THF with butyllithium. The resulting enolether can then be hydrolyzed, e.g. with hydrochloric acid, to the aldehyde IX.

An alcohol X with the non-natural configuration at the methylated C atom in position 20 of vitamin $D_3$, can be obtained by epimerization of the corresponding aldehyde XI with natural configuration, with 1,5-diazabicyclo[4.3.0]non-5-en (DBN) in THF, followed by reduction with sodium borohydride and chromatographic separation of the desired alcohol X.

Compounds of formula X can be prepared as described in the European patent application 0 771 789, as set forth in formula Scheme 1 below:

According to Scheme 1, compound (1) [Synthesis 957 (1993)] is reduced to yield the equatorial alcohol (2), which is transformed to (4) via the thiocarbamate (3). Compound (4) can be hydroborated to yield (5). Oxydation of the alcohol, e.g., with pyridiniumchlorochromate or TPAP and equilibration with potassium-t-butoxide yields (6), which can be reduced to give compound (7). Acetylation of (7) and cleavage of the tert.-butyl ether function yields (8) which is oxidized and deacylated to yield ketoalcohol (9). For build-up of the vitamin $D_3$ side chain the alcohol group of (9) is suitably protected, e.g., by a silyl ether protecting group Z, preferably the tert-butyl-dimethyl-silyl group, to obtain (10).

The ketone (10) is converted by a Wittig reaction into compound (11) from which (12) with natural configuration is obtained as major product by an ene reaction with paraformaldehyde and dimethylaluminum chloride, or with paraformaldehyde and $BF_3.Et_2O$. Optionally, the non-natural epimer of (12) which is formed as side product can also be isolated by chromatography. Catalytic hydrogenation of (12) or of its epimer gives (13) or its epimer, respectively.

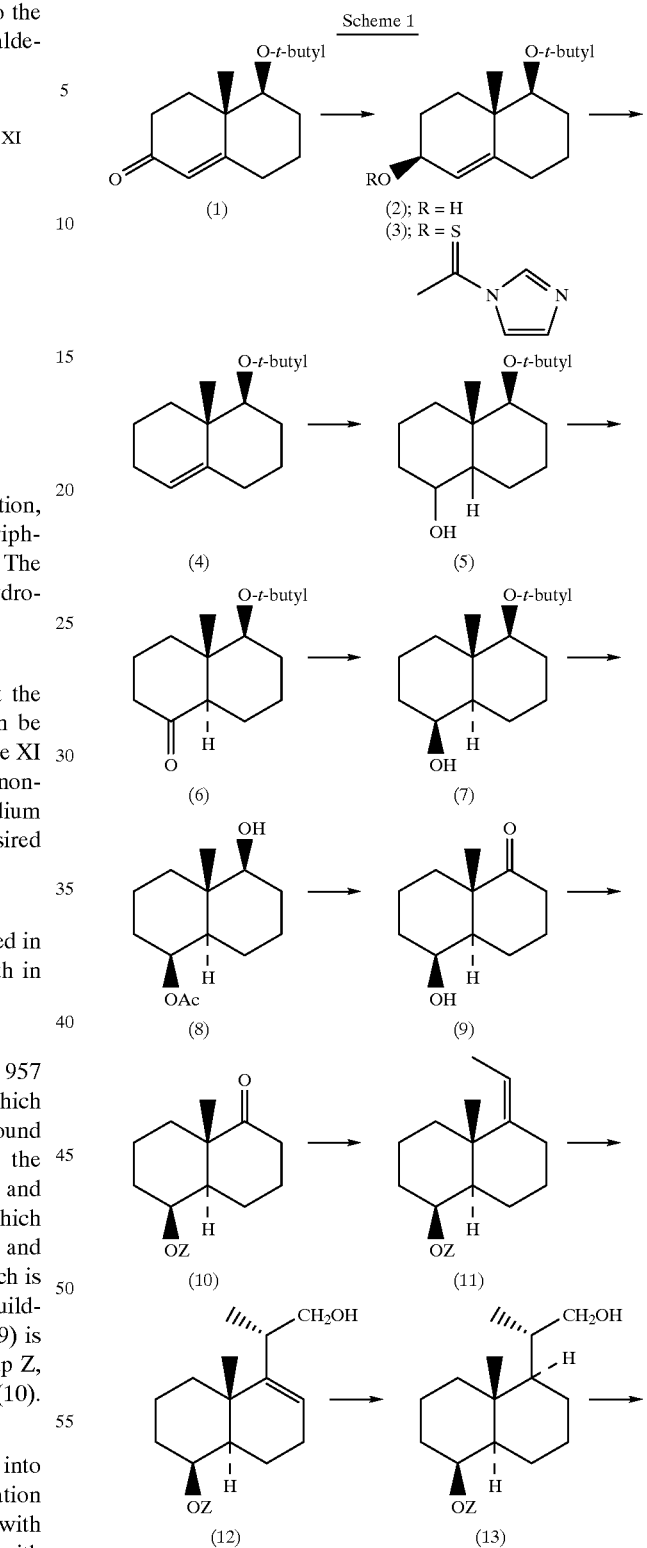

The phosphine oxides of formula III are known or can be obtained in a manner analogous to the known compounds. Thus, those wherein C(R,R) is $CH_2$ can be prepared as shown in formula Scheme 2 below:

Scheme 2

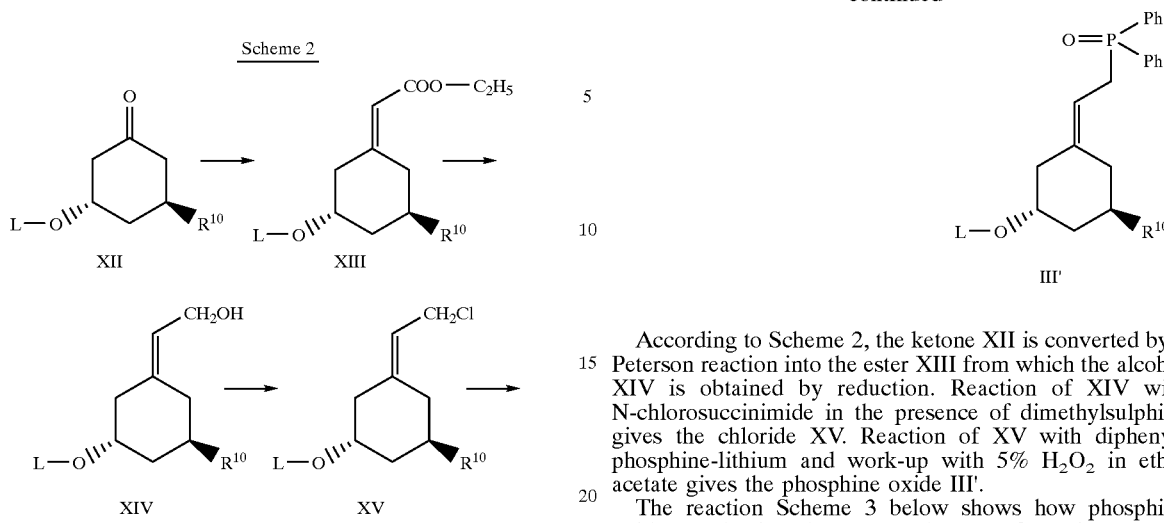

According to Scheme 2, the ketone XII is converted by a Peterson reaction into the ester XIII from which the alcohol XIV is obtained by reduction. Reaction of XIV with N-chlorosuccinimide in the presence of dimethylsulphide gives the chloride XV. Reaction of XV with diphenyl-phosphine-lithium and work-up with 5% $H_2O_2$ in ethyl acetate gives the phosphine oxide III'.

The reaction Scheme 3 below shows how phosphine oxides III having the unnatural 3α-configuration can be prepared according to the methods described in Tetrahedron Letters 1992:2455 and 4364, and 1996:5589. When starting from (S)-epichlorhydrine instead of (R)-epichlorhydrine utilized as starting material in Scheme 3, one obtains unnatural 1β-configurated phosphine oxide.

In Scheme 3, TBHP stands for tert-butyl-hydroperoxide, TBDPS for tert-butyl-diphenylsilyl, PPTS for pyridinium p-toluenesulfonate, Red-Al for sodium dihydro-bis(2-methoxyethoxy)aluminate, and NCS for N-chlorosuccinimide.

Scheme 3

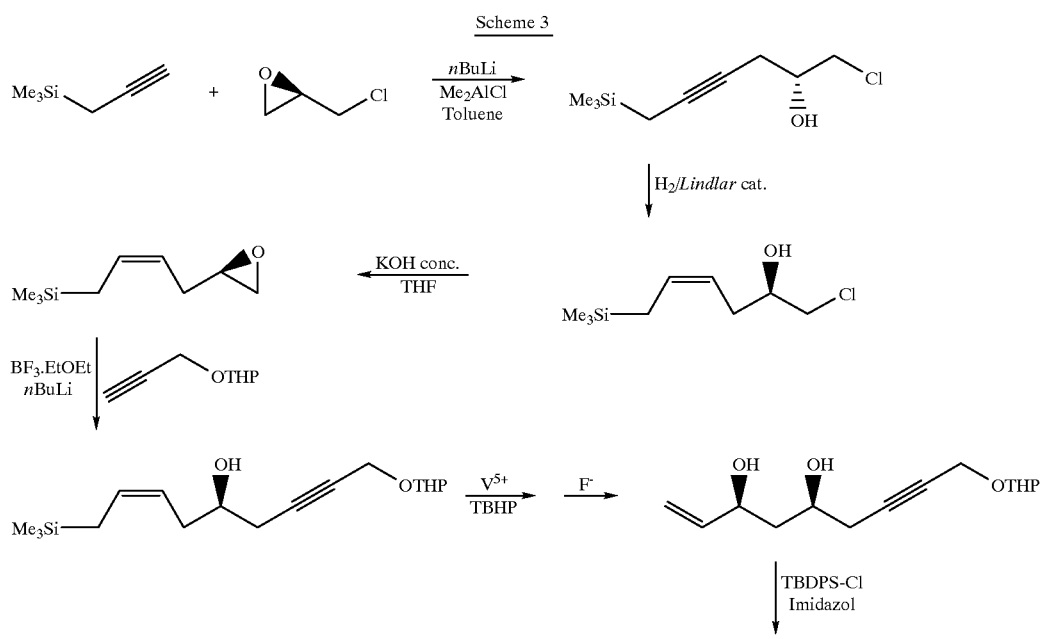

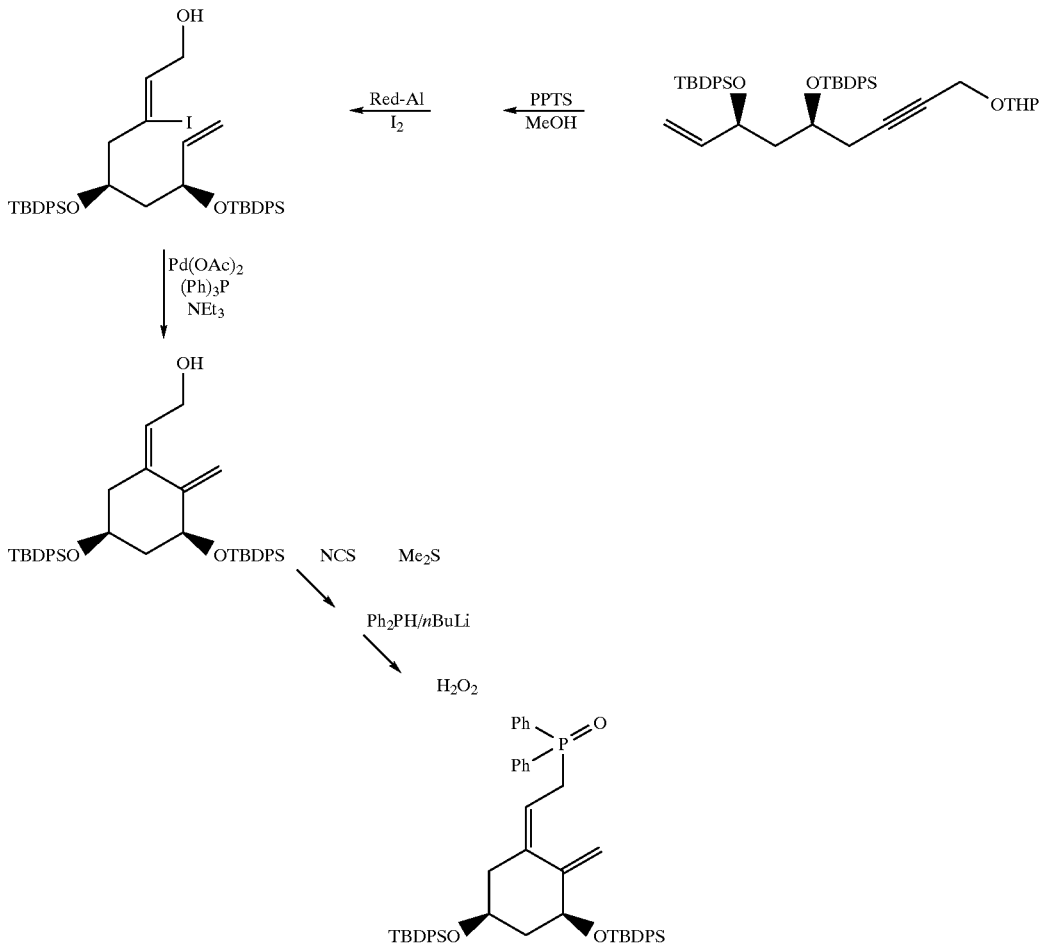

EXAMPLE 1 a) (S)-2-[(4aR,5S,8aS)-5-(tert-Butyl-dimethyl-silanyloxy)-8a-methyl-3,4,4a,5,6,7,8,8a-octa-iydro-naphthalen-1-yl]-propionaldehyde Swern reagent was prepared at −70° C. by adding slowly 0.730 ml (10.3 mmol) of abs. DMSO, dissolved in 3 ml of abs. CH$_2$Cl$_2$, to a solution of 0.406 ml (4.72 mmol) of oxalylchloride in 12 ml of CH$_2$Cl$_2$. 15 Minutes later, 1.50 g (4.42 mmol) of (S)-2-[(4aR,5S,8aS)-5-(tert-butyl-dimethylsilanyloxy)-8a-methyl-3,4,4a,5,6,7,8,8a-octahydro-naphthalen-1-yl]-propan-1-ol (EP 0771789, Example 13), dissolved in 5 ml of CH$_2$Cl$_2$, was slowly added (strongly exothermic). After 0.25 h, 2.06 ml (14.8 mmol) of NEt$_3$ was added dropwise and the temperature allowed to reach −35° C. The reaction was quenched by pouring onto crushed ice/NH$_4$Cl, extracted twice with ether, washed with water and brine, dried over sodium sulfate and evaporated to dryness. Flash chromatography (SiO$_2$, hexane/AcOEt=97/3) afforded 1.368 g of the epimerically pure title compound as colorless oil.

MS: (M)$^+$336, (M-CH$_3$)$^+$321, (M-tBu)$^+$279.

b) (R)-3-[(4aR,5S,8aS)-5-(tert-Butyl-dimethyl-silanyloxy)-8a-methyl-3,4,4a,5,6,7,8,8a-octahydro-naphthalen-1-yl]-butyraldellyde 2.79 g (8.14 mmol) of (methoxymethyl)-triphenylphosphonium chloride was suspended in 16 ml of abs. THF and deprotonated at −10° C. with 7.33 mmol of sec BuLi (5.64 ml, 1.3M, cyclohexane). After cooling to at −78° C., 1.368 g (4.064 mmol) of (S)-2-[(4aR,5S,8aS)-5-(tert-butyl-dimethylsilanyloxy)-8a-methyl-3,4,4a ,5,6,7,8,8a-octa-hydro-naphthalen-1-yl]-propionaldehyde, dissolved in 8 ml of abs. THF, was added and the mixture kept for 1 h at that temperature. Twice partitioning between hexane and EtOH/water=8/2, drying of the hexane layer and removing of the solvents i. V. yielded 1.99 g of a crude mixture of E/Z-enolethers which was hydrolyzed as follows: it was treated at 0° C. with 18 ml of THF and 7.0 ml of 25% HCl and then allowed to react at RT for 2.5 h. Pouring onto crushed ice/NaHCO$_3$, twofold extraction with ether, washing with water, drying over sodium sulfate, evaporation to dryness, and flash chromatography (SiO$_2$, hexane/AcOEt=97/3) afforded 1.193 g of the epimerically pure title product as colorless oil.

MS: (M)$^+$350, (M-tBu)$^+$293.

c) tert-Butyl-[(1S,4aS,8aR)-5-((R)-4,4-dibromo-1-methyl-but-3-enyl)-4a-methyl-1,2,3,4,4a,7,8,8a-octahydro-naplthalen-1-yloxy]-dimethyl-silane 1.82 g (5.49 mmol) of CBr$_4$ in 13 ml of abs. CH$_2$Cl$_2$ was treated with 2.76 g (10.99 mmol) of triphenylphosphin at −10° C. After 5 minutes, 970 mg (2.77 mmol) of (R)-3-[(4aR,5S,8aS)-5-(tert-butyl-dimethyl-silanyloxy)-8a-methyl-3,4,4a,5,6,7,8,8a-octahydro-naphthalen-1-yl]-butyraldehyde, dissolved in 5 ml of abs. CH$_2$Cl$_2$, was added and the temperature rised to 0°. 15 Minutes later, the reaction mixture was partitioned between hexane and EtOH/water=8/2, the upper layers dried over sodium sulfate, and the solvents removed i. V. Flash chromatography (SiO$_2$, hexane) delivered 1.48 g of the title compound as colorless oil, sufficient pure for the next step.

MS: (M)⁺504, 506 (2 Br), (M-tBu)⁺447, 449 (2 Br).

d) (R)-6-[(4aR,5S,8aS)-5-(tert-Butyl-dimethyl-silanyloxy)-8a-methyl-3,4,4a,5,6,7,8,8a-octahydro-naphthalen-1-yl]-2-methyl-hept-3-yn-2-ol 1.48 g (£2.77 mmol) of tert-Butyl-[(1S,4aS,8aR)-5-((R)-4,4-dibromo-1-methyl-but-3-enyl)-4a-methyl-1,2,3,4,4a,7,8,8a-octahydro-naphthalen-1-yloxyl-dimethyl-silane was dissolved in 16 ml of abs. THF and cooled down to −78°. 5.53 ml of nBuLi (1.5M, hexane) was slowly added and the temperature maintained for 1 h. 1.0 ml (13.6 mmol) of acetone, dissolved in 2 ml of abs. THF, was then added to the resultant acetylide-solution and allowed to react for 30 minutes. The reaction was quenched by pouring onto crushed ice/NH₄Cl, extracted twice with ether, washed with water and brine, dried over sodium sulfate and evaporated to dryness. Flash chromatography (SiO₂, hexane/AcOEt=9/1) afforded 866 mg of the title compound as colorless oil.

e) (1S,4aS,8aR)-5-[(R)-5-Hydroxy-1,5-dimethyl-hex-3-ynyl]-4a-methyl-1,2,3,4,4a,7,8,8a-octahydro-naphthalen-1-ol 5.43 g (17.2 mmol) of nBu₄NF.3H₂O in 10 ml of THF was carefully dried by stirring during 2 h at RT over 7.5 g of 3 Å molecular sieve. This solution was then added to 866 mg (2.14 mmol) of (R)-6-[(4aR,5S,8aS)-5-(tert-butyl-dimethyl-silanyloxy)-8a-methyl-3,4,4a,5,6,7,8,8a-octahydro-naphthalen-1-yl]-2-methyl-hept-3-yn-2-ol and the mixture kept for 24 h at 55°. The reaction mixture was then poured onto crushed ice, extracted twice with ether, washed with water and brine, dried over sodium sulfate, and evaporated to dryness. Flash chromatography (SiO₂, hexane/AcOEt=7/3) afforded 590 mg of the title compound as colorless oil.

MS: (M)⁺290, (M-H₂O)⁺272, (M-H₂O-CH₃)⁺257.

f) (4aS,8aR)-5-((R)-5-Hydroxy-1,5-dimethyl-hex-3-ynyl)-4a-methyl-3,4,4a,7,8,8a-hexahydro-2H-naphthalen-1-one 590 mg (2.03 mmol) of (1S,4aS,8aR)-5-[(R)-5-Hydroxy-1,5-dimethyl-hex-3-ynyl]-4a-methyl-1,2,3,4,4a,7,8,8a-octahydro-naphthalen-1-ol was dissolved in 10 ml of abs. CH₂Cl₂ and oxidized with 1.91 g (5.08 mmol) of pyridinium dichromate during 2 h at ambient temperature. Filtration over Celite, evaporation to dryness, and flash chromatography (SiO₂, Hexane/AcOEt=7/3) produced 446 mg of the title compound as colorless oil.

g) (4aS,8aR)-5-[(R)-5-Trimethylsilanyloxy-1,5-dimethyl-hex-3-ynyl]-4a-methyl-1,2,3,4,4a,7,8,8a-octahydro-naphthalen-1-one 446 mg (1.55 mmol) of (4aS,8aR)-5-((R)-5-hydroxy-1,5-dimethyl-hex-3-ynyl)-4a-methyl-3,4,4a,7,8,8a-hexahydro-2H-naphthalen-1-one in 12 ml of abs. CH₂Cl₂ was treated with 2.03 ml (9 eq.) of TMS-imidazole and kept at RT for 24 h. Pouring onto crushed ice, twofold extraction with ether, washing with water and brine, and drying over sodium sulfate left a crude product, which was purified by flash chromatography (SiO₂, hexane/AcOEt=9/1). Thereby, 561 mg of the title compound was obtained as colorless oil.

MS: (M)⁺360, (M-CH₃)⁺345.

h) (4aS,8aS)-4-{(E)-2-[(3R,5R)-3,5-Bis-(tert-butyl-dimethyl-silanyloxy)-cyclohexylidene]-ethylidene}-8-((R)-1,5-dimethyl-5-trimethylsilanyloxy-hex-3-ynyl)-8a-methyl-1,2,3,4,4a,5,6,8a-octahydro-naphthalene 511 mg (0.893 mmol) of carefully dried (3R,5R)-[2-[3,5-bis-(t-butyl-dimethyl-silanyloxy)-cyclohexylidene]-ethyl]-diphenyl-phosphine oxide (*Tetrahedron Lett.* 32, 7663 (1991)) was dissolved in 5 ml of abs. THF and treated at −78° with 0.65 ml of nBuLi (1.55M, hexane). 15 Minutes later, 179 mg (0.496 mmol) of (4aS,8aR)-5-[(R)-5-trimethylsilanyloxy-1,5-dimethyl-hex-3-ynyl]-4a-methyl-1,2,3,4,4a,7,8,8a-octahydro-naphthalen-1-one, dissolved in 0.5 ml of abs. THF, was added to the deep red solution and kept for 1 h at −78° and for 0.75 h at 0°. The reaction mixture was then poured onto crushed ice/KH₂PO₄, extracted twice with ether, washed with water and brine, dried over sodium sulfate, and the solvents carefully removed i.V. Flash chromatography (SiO₂, hexane/AcOEt=9/1) afforded 108 mg of the title compound as colorless oil, besides 122 mg of recovered ketone in the more polar fractions.

i) (7E)-(1R,3R)-D-Homo-19-nor-9,10-seco-cholesta-5,7,17-trien-23-yne-1,3,25-triol 573 mg (1.82 mmol) of nBu₄NF.3H₂O in 4 ml of THF was carefully dried by stirring during 1 h at RT over 0.5 g of 3 Å molecular sieve. This solution was then added to 108 mg (0.151 mmol) of (4aS,8aS)-4-{(E)-2-[(3R,5R)-3,5-bis-(tert-butyl-dimethyl-silanyloxy)-cyclohexylidene]-ethylidene}-8-((R)-1,5-dimethyl-5-trimethylsilanyloxy-hex-3-ynyl)-8a-methyl-1,2,3,4,4a,5,6,8a-octahydro-naphthalene which had been dissolved in 1 ml of abs. THF. After stirring for 1 h at 50° the reaction mixture was poured onto crushed ice/NH₄Cl, extracted twice with ether, washed with brine, dried over sodium sulfate and evaporated to dryness. Flash chromatography (SiO₂, AcOEt) yielded 61 mg of the title compound as white foam.

CI-MS: (M+NH₄)⁺430, (M+H)⁺413; NMR: (1H, d, TMS) 0.82 (s, 3H), 1.10 (d, 3H), 1.48(s, 6H), 1.25–2.55 (m, 21H), 2.72–2.92 (m, 2H), 4.00–4.18 (m, 2H), 5.38 (m, 1H), 5.88 (d, 1H), 6.31 (m,1H).

EXAMPLE 2

In analogy to example 1 but using, as appropriate, in step a](R)-2-[(4aR,5S,8aS)-5-(tert-butyl-dimethyl-silanyloxy)-8a-methyl-3,4,4a,5,6,7,8,8a-octahydro-naphthalen-1-yl]-propan-1-ol instead of the (S)-epimer, in step d] hexafluoroacetone, cyclohexanone, cyclopentanone or diethyl ketone instead of acetone, and in step h] (Z)-(3S, 5R)-[2-[5-(t-butyldimethyl-silanyloxy)-3-fluoro-2-methylene-cyclohexylidene]-ethyl]-diphenyl-phosphine oxide, (Z)-(5S)-[2-[5-(t-butyldimethyl-silanyloxy)-2-methylene-cyclohexylidene]-ethyl]-diphenyl-phosphine oxide, (Z)-(3S,5R)-[2-[3,5-bis-(t-butyldimethyl-silanyloxy)-2-methylene-cyclohexylidene]-ethyl]-diphenyl-phosphine oxide, (Z)-(3R,5R)-[2-[3,5-bis-(t-butyldiphenylsilanyloxy)-2-methylene-cyclohexylidene]-ethyl]-diphenyl-phosphine oxide, or (Z)-(3S,5S)-[2-[3,5-bis-(t-butyldiphenyl-silanyloxy)-2-methylenecyclohexylidene]-ethyl]-diphenyl-phosphine oxide, respectively, instead of (3R,5R)-[2-[3,5-bis-(t-butyldimethyl-silanyloxy)-cyclohexylidene]-ethyl]-diphenyl-phosphine oxide, there were prepared:

2.1 (5Z,7E)-(1S,3R)-1,26,26,26,27,27,27-heptafluoro-D-homo-9,10-seco-cholesta-5,7,10(19),17-tetraen-23-yne-3,25-diol as white foam

MS: (M)⁺534, (M-HF)⁺514.

NMR: (19F, d, CFCl₃) −78.2 (CF₃), −175.7 (HCF).

2.2 (5Z,7E)-(3S)-D-Homo-9,10-seco-cholesta-5,7,10(19),17-tetraen-23-yne-3,25-diol as white foam

MS: (M)⁺408, (M-H₂O-CH₃)⁺375;

IR: (cm⁻¹) 3346, 2923, 2853, 2250, 1456, 1375, 1166, 1051, 947, 890; NMR: (1H, d, TMS) 0.82 (s, 3H), 1.10 (d, 3H), 1.48 (s, 6H), 1.25–2.5 (m, 20H), 2.59 (br dd, 1H), 2.89 (m, 1H), 3.95 (m, 1H), 4.84 (br s, 1H), 5.07 (br s, 1H), 5.37 (br t, 1H), 6.04 (d, 1H), 6.23 (d, 1H).

2.3 (5Z,7E)-(1S,3R)-D-Homo-9,10-seco-cholesta-5,7,10(19),17-tetraen-23-yne-1,3,25-triol as white solid, mp. 108–111° (dec.)

MS: (M)⁺424, (M-H₂O)⁺424; NMR: (1H, d, TMS) amongst others 0.82 (s, 3H), 1.11 (d, 3H), 1.48 (s, 6H), 4.23

(m, 1H), 4.45 (m, 1H), 5.02 (br s, 1H), 5.35 (br s, 1H), 5.37 (br t, 1H), 6.04 (d, 1 h), 6.39 (d, 1H).

2.4 (5Z,7E)-(1S,3R,20S)-D-Homo-9,10-seco-cholesta-5,7,10(19),17-tetraen-23-yne-1,3,25-triol as white foam CI-MS: $(M+Na)^+447$, $(M+NH_4)^+442$; NMR: (1H, d, TMS) amongst others 0.80 (s, 3H), 1.10 (d, 3H), 1.51 (s, 6H), 4.23 (m, 1H), 4.46 (m, 1H), 5.01 (br s, 1H), 5.34 (br s, 1H), 5.41 (br t, 1H), 6.03 (d, 1H), 6.37 (d, 1H).

2.5 (7E)-(1R,3R,20S)-D-Homo-19-nor-9,10-seco-cholesta-5,7,17-trien-23-yne-1,3,25-triol as colorless foam MS: $(M)^+412$, $(M-H_2O)^+394$; NMR: (1H, d, TMS) amongst others 0.80 (s, 3H), 1.11 (d, 3H), 1.51 (s, 6H), 4.10 (m, 2H), 5.43 (br t, 1H), 5.87 (d, 1H), 6.32 (d, 1H).

2.6 (5Z,7E)-(3S,20S)-D-Homo-9,10-seco-cholesta-5,7,10(19),17-tetraen-23-yne-3,25-diol as white foam MS: $(M)^+408$, $(M-H_2O)^+390$, $(M-H_2O-CH_3)^+375$; NMR: (1H, d, TMS) amongst others 0.80 (s, 3H), 1.11 (d, 3H), 1.51 (s, 6H), 3.96 (m, 1H), 4.84 (br s, 1H), 5.06 (br s, 1H), 5.41 (t, 1H), 6.05 (d, 1H), 6.24 (d, 1H).

2.7 (7E)-(1R,3R)-24-(1-Hydroxy-cyclohexyl)-D-homo-9,10-seco-chola-5,7,17-trien-23-yne-1,3-diol as white solid, mp. 103–105°

MS: $(M)^+452$, $(M-H_2O)^+434$, $(M-H_2O-CH_3)^+419$; IR: $(cm^{-1})$ 3345, 2926, 2854, 2245, 1454, 1376, 1051, 964; NMR: (1H, d, TMS) amongst others 0.82 (s, 3H), 1.13 (d, 3H), 4.0–4.25 (m, 2H), 5.39 (t, 1H), 5.88 (d, 1H), 6.31 (d, 1H).

2.8 (7E)-(1R,3R)-26,26,26,27,27,27-Hexafluoro-D-homo-9,10-seco-cholesta-5,7,17-trien-23-yne-1,3,25-triol as colorless oil MS: $(M)^+520$; IR: $(cm^{-1})$ 3355, 2923, 2853, 2250, 1455, 1376, 1224, 1157; NMR: (1H, d, TMS) amongst others 0.81 (s, 3H), 1.13 (d, 3H), 4.0–4.22 (m, 2H), 5.40 (br t, 1H), 5.89 (d, 1H), 6.31 (d, 1H).

2.9 (7E)-(1R,3R)-17a,26a,27a-Trihomo-9,10-seco-cholesta-5,7,17-trien-23-yne-1,3,25-triol as colorless oil MS: $(M)^+440$, $(M-H_2O-CH_3)^+407$; IR: $(cm^{-1})$ 3350, 2926, 2245, 1045, 962; NMR: (1H, d, TMS) amongst others 0.81 (s, 3H), 1.01 (t, 6H), 1.13 (d, 3H), 3.98–4.22 (m, 2H), 5.39 (br t, 1H), 5.88 (d, 1H), 6.31 (d, 1H).

2.10 (5Z,7E)-(1S,3R)-24-(1-Hydroxy-cyclohexyl)-D-homo-9,10-seco-chola-5,7,10(19),17-tetraen-23-yne-1,3-diol as colorless oil MS: $(M)^+464$, $(M-H_2O)^+446$; NMR: (1H, d, TMS) amongst others 0.82 (s, 3H), 1.12 (d, 1H), 4.23 (m, 1H), 4.45 (m, 1H), 5.01 (br s, 1H), 5.34 (br s, 1H), 5.38 (br t, 1H), 6.04 (d, 1H), 6.38 (d, 1H).

2.11 (5Z,7E)-(3S)-24-(1-Hydroxy-cyclohexyl)-D-homo-9,10-seco-chola-5,7,10(19),17-tetraen-23-yne-3-ol as white foam MS: $(M)^+448$, $(M-H_2O)^+430$, $(M-H_2O-CH_3)^+415$; IR: $(cm^{-1})$ 3425, 2933, 2240; NMR: (1H, d, TMS) amongst others 0.82 (s, 3H), 1.12 (d, 3H), 3.95 (m, 1H), 4.84 (br s, 1H), 5.06 (br s, 1H), 5.38 (br t, 1H), 6.05 (d, 1H), 6.23 (d, 1H).

2.12 (5Z,7E)-(1S,3R)-17a,26a,27a-Trihomo-9,10-seco-cholesta-5,7,10(19),17-tetraen-23-yne-1,3,25-triol as white foam MS: $(M)^+452$, $(M-H_2O-CH_3)^+419$; IR: $(cm^{-1})$ 3350, 2935, 2240, 1055; NMR: (1H, d, TMS) amongst others 0.81 (s, 3H), 1.01 (t, 6H), 1.12 (d, 3H), 4.24 (m, 1H), 4.45 (m, 1H), 5.01 (br s, 1H), 5.34 (br s, 1H), 5.37 (br t, 1H), 6.04 (d, 1H), 6.38 (d, 1H).

2.13 (5Z,7E)-(3S)-17a,26a,27a-Trihomo-9,10-seco-cholesta-5,7,10(19),17-tetraen-23-yne-3,25-diol as white foam MS: $(M)^+436$, $(M-H_2O-CH_3)^+403$; IR: $(cm^{-1})$ 3355, 2938, 2240, 1444, 1055, 896; NMR: (1H, d, TMS) amongst others 0.81 (s, 3H), 1.01 (t, 6H), 1.12 (d, 3H), 3.95 (m, 1H), 4.84 (br s, 1H), 5.07 (br s, 1H), 5.37 (br t, 1H), 6.05 (d, 1H), 6.23 (d, 1H).

2.14 (7E)-(1R,3R)-24-(1-Hydroxy-cyclopentyl)-D-homo-9,10-seco-chola-5,7,17-trien-23-yne-1,3-diol as white foam MS: $(M)^+438$, $(M-H_2O)^+420$, $(M-H_2O-CH_3)^+405$; IR: $(cm^{-1})$ 3360, 2923, 2854, 2255, 1455, 1376; NMR: (1H, d, TMS) amongst others 0.82 (s, 3H), 1.11 (d, 3H), 3.99–4.21 (m, 2H), 5.39 (br t, 1H), 5.87 (d, 1H), 6.31 (d, 1H).

2.15 (5Z,7E)-(1S,3R)-24-(1-Hydroxy-cyclopentyl)-D-homo-9,10-seco-chola-5,7,10(19),17-tetraen-23-yne-1,3-diol as white foam MS: $(M+H)^+451$, $(M-H_2O)^+432$; IR: $(cm^{-1})$ 3360, 2923, 2854, 2255, 1455, 1376; NMR: (1H, d, TMS) amongst others 0.82 (s, 3H), 1.11 (d, 3H), 3.99–4.21 (m, 2H), 5.39 (br t, 1H), 5.87 (d, 1H), 6.31 (d, 1H).

2.16 (5Z,7E)-(1S,3S)-D-Homo-9,10-seco-cholesta-5,7,10(19),17-tetraen-23-yne-3,25-diol as white solid, mp. 68–72°.

MS: $(M)^+424$, $(M-H_2O)^+406$, $(M-H_2O-CH_3)^+391$; NMR: (1H, d, TMS) amongst others 0.82 (s, 3H), 1.10 (d, 3H), 1.48 (s, 6H), 4.09 (m, 1H), 4.35 (br q, 1H), 5.03 (br s, 1H), 5.31 (br s, 1H), 5.37 (br t, 1H), 6.05 (d, 1H), 6.44 (d, 1H).

2.17 (5Z,7E)-(1S,3S)-26,26,26,27,27,27-Hexafluoro-D-homo-9,10-seco-cholesta-5,7,10(19),17-tetraen-23-yne-1,3,25-triol as white foam MS: $(M)^+532$, $(M-H_2O)^+514$; NMR: (1H, d, TMS) amongst others 0.81 (s, 3H), 1.12 (d, 3H), 3.41 (br s, 1H, OH), 4.08 (m, 1H), 4.34 (br q, 1H), 5.02 (br s, 1H), 5.32 (br s, 1H), 5.39 (br t, 1H), 6.05 (d, 1H), 6.44 (d, 1H).

2.18 (5Z,7E)-(1S,3R)-1-Fluoro-D-homno-9,10-seco-cholesta-5,7,10(19),17-tetraen-23-yne-3,25-diol as white foam MS: $(M)^+426$, $(M-H_2O-CH_3)^+393$; NMR: (1H, d, TMS) amongst others 0.82 (s, 3H), 1.11 (d, 3H), 1.48 (s, 6H), 4.23 (m, 1H), 5.13 (br s, 1H), 5.14 (ddd, 1H, CHF), 5.38 (m, 1H), 5.41 (br s, 1H), 6.05 (d, 1H), 6.40 (d, 1H).

2.19 (5Z,7E)-(3S)-24-(1-hydroxycyclopentyl)-D-homo-9,10-seco-chole-5,7,10(19),17-tetraen-23-yne-3-ol as white foam

MS: $(M)^+434$, $(M—H_2O)^+416$, $(M—H_2O-CH^{-3})^+402$.

EXAMPLE 3 a) (S)-2-[(1R,4aR,5S,8aR)-2-[5-(tert-Butyl-dimethyl-silanyloxy)-8a-methyl-decahydro-naphthalen-1-yl]-propionaldehyde Swern reagent was prepared at −60° C. by adding slowly 1.86 ml (26.25 mmol) of abs. DMSO, dissolved in 6 ml of abs. $CH_2Cl_2$, to a solution of 1.03 ml (11.98 mmol) of oxalylchloride in 30 ml of $CH_2Cl_2$. 15 Minutes later, 3.78 g (10.93 mmol) of (S)-2-[(1R,4aR,5S,8aR)-5-(tert-butyl-dimethyl-silanyloxy)-8a-methyl-decahydro-naphthalen-1-yl]-propan-1-ol (EP 0771789, Example 14), dissolved in 12 ml of $CH_2Cl_2$, was slowly added (strongly exothermic). After 0.25 h, 5.24 ml (37.56 mmol) of $NEt_3$ was added dropwise and the temperature allowed to reach −40° C. The reaction was quenched by pouring onto crushed ice/$NH_4Cl$, extracted twice with ether, washed with water and brine, dried over sodium sulfate and evaporated to dryness. Flash chromatography ($SiO_2$, hexane/AcOEt=97/3) afforded 3.32 g of the epimerically pure title compound as colorless oil.

b) (R)-3-[(1R,4aR,5S,8aR) 5-(tert-Butyl-dimethyl-silanyloxy)-8a-methyl-decahydro-napthalen-1-yl]-butyraldehyde 6.73 g (19.64 mmol) of (methoxymethyl)-triphenylphosphonium chloride was suspended in 40 ml of abs. THF and deprotonated at −10° C. with 17.5 mmol of nBuLi (11.3 ml, 1.55M, cyclohexane). After cooling to at −78° C., 3.32 g (9.804 mmol) of (S)-2-[(1R,4aR,5S,8aR)-2-[5-(tert-butyl-dimethyl-silanyloxy)-8a-methyl-decahydro-naphthalen-1-yl]-propionaldehyde, dissolved in 12 ml of abs. THF, was added and the mixture kept for 0.5 h at that temperature. Twice partitioning between hexane and EtOH/water=8/2, drying of the hexane layer and removing of the solvents i.V. yielded 4.4 g of a crude mixture of E/Z-enolethers which was hydrolyzed as follows:

it was treated at 0° C. with 40 ml of THF and 12.5 ml of 25% HCl and then allowed to react at RT for 3 h. Pouring onto crushed ice/NaHCO$_3$, twofold extraction with ether, washing with water and brine, drying over sodium sulfate, evaporation to dryness, and flash chromatography (SiO$_2$, hexane/AcOEt=97/3) gave 2.27 g of the epimerically pure title product as colorless oil.

MS: (M-t-butyl)$^+$295.

c) tert-Butyl-[(1S,4aR,5R,8aR)-5-((R)-4,4-dibromo-1-nethyl-but-3-enyl)-4a-methyl-decahydro-naphthalen-1-yloxy]-dimethyl-silane 4.24 g (12.79 mmol) of CBr$_4$ in 30 ml of abs. CH$_2$Cl$_2$ was treated at −10° C. with 6.43 g (25.58 mmol) of triphenylphosphin. After 5 minutes, 2.27 g (6.44 mmol) of (R)-3-[(1R,4aR,5S,8aR) 5-(tert-butyl-dimethyl-silanyloxy)-8a-methyl-decahydro-naphthalen-1-yl]-butyraldehyde, dissolved in 15 ml of abs. CH$_2$Cl$_2$, was added and stirring continued for 15 minutes. The reaction mixture was then partitioned between hexane and EtOHi/water=8/2, the upper layers dried over sodium sulfate, and the solvents removed i. V. Flash chromatography (SiO$_2$, hexane) delivered 3.05 g of the title compound as colorless oil.

d) (R)-6-[(1R,4aR,5S,8aR)-5-(tert-Butyl-dimethyl-silanyloxy)-8a-methyl-decahydro-naphthalen-1-yl]-2-methyl-hept-3-yn-2-ol 3.05 g (6.00 mmol) of tert-butyl-[(1S,4aR,5R,8aR)-5-((R)-4,4-dibromo-1-methyl-but-3-enyl)-4a-methyl-decahydro-naphthalen-1-yloxy]-dimethyl-silane was dissolved in 35 ml of abs. THF and cooled down to −78°. 11.6 ml of nBuLi (1.55M, hexane) was slowly added and the temperature maintained for 1 h. 2.15 ml (29.3 mmol) of acetone, dissolved in 5 ml of abs. THF, was then added to the resultant acetylide-solution and allowed to react for 30 minutes. The reaction was quenched by pouring onto crushed ice/NH$_4$Cl, extracted twice with ether, washed with water and brine, dried over sodium sulfate and evaporated to dryness. Flash chromatography (SiO$_2$, hexane/AcOEt=9/1) yielded 1.93 g of the title compound as colorless oil.

e) (1S,4aR,5R,8aR)-5-((R)-5-Hydroxy-1,5-dimethyl-hex-3-ynyl)-4a-methyl-decahydro-naphthalen-1-ol 12.0 g (38.0 mmol) of nBu$_4$NF.3H$_2$O in 40 ml of THF was carefully dried by stirring during 2 h at RT over 15 g of 3 Å molecular sieve. This solution was then added to 1.93 g (4.748 mmol) of (R)-6-[(1R,4aR,5S,8aR)-5-(tert-butyl-dimethyl-silanyloxy)-8a-methyl-decahydro-naphthalen-1-yl]-2-methyl-hept-3-yn-2-ol and the mixture kept for 40 h at 55°. The reaction mixture was then poured onto crushed ice, extracted twice with ether, washed with water and brine, dried over sodium sulfate, and evaporated to dryness. Flash chromatography (SiO$_2$, hexane/AcOEt=8/2) afforded 1.22 g of the title compound as white crystals of mp. 134–135°.

MS: (M-CH$_3$)$^+$277, (M-CH$_3$-H$_2$O.)$^+$259.

f) (4aR,5R,8aR)-5-((R)-5-Hydroxy-1,5-dimethyl-hex-3-ynyl)-4a-methyl-octahydro-naphthalen-1-one 1.22 g (4.17 mmol) of (1S,4aR,5R,8aR)-5-((R)-5-hydroxy-1,5-dimethyl-hex-3-ynyl)-4a-methyl-decahydro-naphthalen-1-ol was dissolved in 36 ml of abs. CH$_2$Cl$_2$ and oxidized with 4.72 g (12.51 mmol) of pyridinium dichromate during 2 h at ambient temperature. Filtration overCelite, evaporation to dryness, and flash chromatography (SiO$_2$, Hexane/AcOEt=7/3) produced 860 mg of the title compound as colorless oil.

g) (4aR,5R,8aR)-5-((R)-1,5-Dimethyl-5-trimethylsilanyloxy-hex-3-ynyl)-4a-methyl-octahydro-naphthalen-1-one 860 mg (2.96 mmol) of (4aR,5R,8aR)-5-((R)-5-hydroxy-1,5-dimethyl-hex-3-ynyl)-4a-methyl-octahydro-naphthalen-1-one in 23 ml of abs. CH$_2$Cl$_2$ was treated with 3.89 ml (26.6 mmol) of TMS-imidazole and kept at RT for 4 h. Pouring onto crushed ice, twofold extraction with ether, washing with water and brine, and drying over sodium sulfate left a crude product, which was purified by flash chromatography (SiO$_2$, hexane/AcOEt=9/1). Thereby, 998 mg of the title compound was obtained as colorless oil.

MS: (M-CH$_3$)$^+$347, (M-C$_2$H$_5$.)$^+$333.

h) (4aR,5R,8aS)-1-{(E)-2-[(3R,5R)-3,5-Bis-(tert-butyl-dimethyl-silanyloxy)-cyclohexylidene]-ethylidene}-5-((R)-1,5-dimethyl-5-trimethylsilanyloxy-hex-3-ynyl)-4a-methyl-decahydro-naphthalene 590 mg (1.03 mmol) of carefully dried (3R,5R)-[2-[3,5-bis-(t-butyldimethylsilanyloxy)-cyclohexylidene]-ethyl]-diphenyl-phosphine oxide (*Tetrahedron Lett.* 32, 7663 (1991)) was dissolved in 5 ml of abs. THF and treated at −78° with 0.644 ml of nBuLi (1.6M, hexane). 15 Minutes later, 187 mg (5.15 mmol) of (4aR,5R,8aR)-5-((R)-1,5-dimethyl-5-trimethylsilanyloxy-hex-3-ynyl)-4a-methyl-octahydro-naphthalen-1-one, dissolved in 0.5 ml of abs. THF, was added to the deep red solution and kept for 0.5 h at −78° and for 0.5 h at 0°. The reaction mixture was then poured onto crushed ice/KH$_2$PO$_4$, extracted twice with ether, washed with water and brine, dried over sodium sulfate, and the solvents carefully removed i.V. Flash chromatography (SiO$_2$, hexane/AcOEt=95/5) afforded in the less polar fractions 129 mg of the title compound as colorless oil and in the more polar ones 67 mg of recovered ketone.

i) (7E)-(1R,3R)-D-Homo-19-nor-9,10-seco-cholesta-5,7-dien-23-yne-1,3,25-triol 569 mg (1.80 mmol) of nBu$_4$NF.3H$_2$O in 2 ml of THF was carefully dried by stirring during 2 h at RT over 0.7 g of 3 Å molecular sieve. This solution was then added to 129 mg (0.180 mmol) of (4aR,5R,8aS)-1-((E)-2-[(3R,5R)-3,5-bis-(tert-butyl-dimethyl-silanyloxy)-cyclohexylidene]-ethylidene1-5-((R)-1,5-dimethyl-5-trimethylsilanyloxy-hex-3-ynyl)-4a-methyl-decahydro-naphthalene. After stirring for 2 h at 35–40° the reaction mixture was poured onto crushed ice/NH$_4$Cl, extracted twice with ether, washed with water and brine, dried over sodium sulfate and evaporated to dryness. Flash chromatography (SiO$_2$, iPrOHlhexane=2/8) yielded 72 mg of the title compound as white foam.

MS: (M)$^+$414; IR: (cm$^{-1}$) 3340, 2922, 2854, 2240, 1455, 1377; NMR: (1H, d, TMS) 0.69 (s, 3H), 1.05 (d, 3H), 1.49 (s, 6H), 0.8–2.1 (m, 20H), 2.15–2.30 (m, 3H), 2.49 (br dd, 1H), 2.70–2.89 (m, 2H), 3.99–4.17 (m, 2H), 5.83 (d, 1H), 6.29 (d, 1H).

EXAMPLE 4

In analogy to example 3 but using, as appropriate, in step h] (Z)-(5S)-[2-[5-(t-butyldimethyl-silanyloxy)-2-methylene-cyclohexylidene]-ethyl]-diphenyl-phosphine oxide, (Z)-(3S,5R)-[2-[3,5-bis-(t-butyldimethyl-silanyloxy)-2-methylene-cyclohexylidene]-ethyl]-diphenyl-phosphine oxide, (Z)-(3R,5R)-[2-[3,5-bis-(t-butyldiphenyl-silanyloxy)-2-methylene-cyclohexylidene]-ethyl]-diphenylphosphine oxide, or (Z)-(3S,5S)-[2-[3,5-bis-(t-butyldiphenyl-silanyloxy)-2-methylene-cyclohexylidene]-ethyl]-diphenyl-phosphine oxide instead of (3R,5R)-[2-[3,5-bis-(t-butyldimethyl-silanyloxy)-cyclohexylidene]-ethyl]-diphenyl-phosphine oxide, there were prepared:

4.1 (5Z,7E)-(1R,3R)-D-Homo-9,10-seco-cholesta-5,7,10 (19)-trien-23-yne-1,3,25-triol as white foam MS: (M)$^+$426, (M-H$_2$O.)$^+$408; IR: (cm$^{-1}$) 3340, 2925, 2859, 2240, 1448, 1362, 1065; NMR: (1H, d, TMS) amongst others 0.70 (s, 3H), 1.05 (d, 3H), 1.49 (s, 6H), 2.48 (dd, 1H), 2.57 (br d, 1H), 2.68 (d, 1H), 2.89 (m, 1H), 4.11 (m, 1H), 4.36 (m, 1H), 5.00 (br s, 1H), 5.30 (br s, 1H), 6.03 (d, 1H), 6.43 (d, 1H).

4.2 (5Z,7E)-(1S,3S)-D-Homo-9,10-seco-cholesta-5,7,10 (19)-trien-23-yne-1,3,25-triol as white foam MS: (M)$^+$426, (M-H$_2$O.)$^+$408; NMR: (1H, d, TMS) amongst others 0.69. (s, 3H), 1.05 (d, 3H), 1.49 (s, 6H), 2.44 (dd, 1H), 2.57 (br dd, 1H), 2.89 (m, 1H), 4.07 (m, 1H), 4.33 (m, 1H), 5.00 (br s, 1H), 5.31 (br s, 1H), 6.00 (d, 1H), 6.43 (d, 1H).

4.3 (5Z,7E)-(1S,3R)-D-Homo-9,10-seco-cho lest a-5,7,10 (19)-trien-23-yne-1,3,25-triol as white foam MS: (M)$^+$426, (M-H$_2$O.)$^+$408; IR: (cm$^{-1}$)3314, 2926, 2859, 2237, 1377, 1359, 1167, 1045, 954; NMR: (1H, d, TMS) amongst others 0.69. (s, 3H), 1.05 (d, 3H), 1.49 (s, 6H), 2.61 (Hr dd, 1H), 2.88 (m, 1H), 4.24 (m, 1H), 4.44 (m, 1H), 5.01 (br s, 1H), 5.34 (br s, 1H), 5.99 (d, 1H), 6.37 (d, 1H).

4.4 (5Z,7E)-(3S)-D-Homo-9,10-seco-cholesta-5,7,10 (19)-trien-23-yne-3,25-diol as white crystals of mp. 146–147°

MS: (M)$^+$410, (M-H$_2$O.)$^+$392, (M-CH$_3$-H$_2$O.)$^+$377; IR: (cm$^{-1}$) 3370, 2924, 2855, 2240, 1458, 1377, 1365, 1169, 1051, 955; NMR: (1H, d, TMS) amongst others 0.69. (s, 3H), 1.05 (d, 3H), 1.49 (s, 6H), 2.58 (br dd, 1H), 2.88 (m, 1H), 3.95 (m, 1H), 4.82 (br s, 1H), 5.06 (br s, 1H), 6.00 (d, 1H), 6.22 (d, 1H).

REFERENCE EXAMPLE 5

The (Z)-(3S,5)-[2[-3,5-bis-(tert-butyl-diphenyl-silanyloxy)-2-methylene-cyclohexylidene]-ethyl]-diphenyl-phosphine oxide utilized in Examples 2 and 4 was obtained as follows:

a) 14.11 g (126 mmol) of propargyltrimethylsilane was dissolved in 125 ml of abs. toluene and cooled to –17°. 81.1 ml of nBuLi (1.55M, hexane) was slowly added while keeping the temperature below –5°. 5 Minutes later, 126 ml of Me$_2$AlCl (1M, hexane) was added to this solution of the Li-acetylide. The temperature was then lowered to –45° and 6.90 ml of (R)-epichlorohydrine (88 mmol), dissolved in 50 ml of toluene, was added. The cooling bath was then removed and the reaction mixture allowed to reach ambient temperature during 24 h. After careful quenching with icecold water and filtration, the product was extracted with ether, washed with NH$_4$Cl, dried over sodium sulfate and the solvents removed i. V. Flash chromatography (SiO$_2$, hexane/AcOEt=86/14) yielded 12.01 g of (R)-1-chloro-6-trimethylsilanyl-hex-4-yn-2-ol as colorless oil, 97% pure according to GC.

MS: (M+H)$^+$205, (M-CH$_3$)$^+$189, (M-Cl)$^+$169.

b) 13.04 g (63.7 mmol) of (R)-1-Chloro-6-trimethylsilanyl-hex-4-yn-2-ol was dissolved in 260 ml of abs. EtOH and hydrogenated, in the presence of 9 drops of quinoline, over 1.70 g of Lindlar catalyst at ambient temperature and 1 atm of H$_2$. The progress of the reaction was followed by GC. After 2 h the reaction mixture was filtered and the solvent removed i.V. Short flash chromatography (SiO$_2$, hexane/AcOEt=85/15) afforded 12.97 g of (Z)-(R)-1-chloro-6-trimethylsilanyl-hex-4-en-2-ol as colorless oil.

MS: (M)$^+$206, (M-HOSi(CH$_3$)$_3$)$^+$116.

c) 12.97 g (62.7 mmol) of (Z)-(R)-1-Chloro-6-trimethylsilanyl-hex-4-en-2-ol was dissolved in 215 ml of abs. THF. A solution of 60.34 g (1.08 mol) of KOH in 61 g of water was added ant the heterogeneous mixture stirred at 30° for 24h, until GC analysis indicated the disappearance of the starting chlorohydrine. The reaction mixture was then poured onto crushed ice/NH$_4$Cl, extracted with ether, dried over sodium sulfate, and the solvents removed i.V. Thereby, 10.5 g of (Z)-(R)-trimethyl-(4-oxiranyl-but-2-enyl)-silane was isolated, 93% pure according to GC, which was used as such for the next step.

d) 24.5 ml (174 mmol) of Tetrahydro-2-(2-propynyloxy) 2H-pyran was dissolved in 285 ml of abs. THF and deprotonated at –13°–-6° by adding slowly 112 ml of nBuLi (1.55M, hexane). 20 Minutes later, the solution was cooled to –75° and 21.85 ml of BF$_3$.EtOEt was added. Afterwards, 10.51 g of (Z)-(R)-trimethyl-(4-oxiranyl-but-2-enyl)-silane, dissolved in 96 ml of abs. THF, was added within 75 minutes while maintaining the temperature below –70°. The reaction mixture was kept for another 50 minutes at this temperature and then poured onto crushed ice/NaHCO$_3$, extracted with ether, washed with brine, dried over sodium sulfate and evaporated to dryness. Flash chromatography (SiO$_2$, hexane/AcOEt=8/2) produced 17.83 g of (Z)-(5R)-9-(tetrahydro-pyran-2-yloxy)-1-trimethyl-silanyl-non-2-en-7-yn-5-ol as colorless oil (1:1 epimeric mixture).

e) 17.83 g (57.4 mmol) of (Z)-(5R)-9-(tetrahydro-pyran-2-yloxy)-1-trimethylsilanyl-non-2-en-7-yn-5-ol was dissolved in 210 ml of abs. toluene. At –15°, 30.6 ml t-butyl-hydroperoxide (3M, toluene) was added, followed by 761 mg (5 mol%) of vanadium-oxyacetylacetonate. The temperature was then rised within 16 h to 220. TLC indicated the disappearance of starting olefin. While cooling in an ice bath, 13.5 ml (115 mmol) of trimethylphosphite was added in order to destroy the excess of hydroperoxide. 90 minutes later, a solution of 39.8 g of dry TBAF in 125 ml of THF was added and the reaction mixture kept for 90 minutes at RT. The homogeneous solution was then poured onto crushed ice, extracted with AcOEt, washed with water, dried over sodium sulfate and evaporated to dryness. Flash chromatography (SiO$_2$, hexane/AcOEt=6/4) yielded 10.40 g of (3S, 5S)-9-(tetrahydro-pyran-2-yloxy)-non-1-en-7-yne-3,5-diol as slightly yellow oil (1:1 epimeric mixture).

MS (CI): (M+NH$_4$)$^+$272, (M+Na)$^+$277.

f) 10.40 g (40.9 mmol) of (3S,5S)-9-(tetrahydro-pyran-2-yloxy)-non-1-en-7-yne-3,5-diol was dissolved in 30 ml of abs. DMF and treated successively with 18.9 g (6.8 eq.) of imidazole and 35.5 ml (3.4 eq.) of tert-butyl-chloro-diphenylsilane. After stirring for 20 h at 40°, the reaction mixture was poured onto crushed ice/EtOEt. Usual workup followed by flash chromatography (SiO$_2$, hexane/AcOEt= 96/6) gave 25.16 g of (5S,7S)-2-[5,7-bis-(tert-butyl-diphenyl-silanyloxy)-non-8-en-2-ynyloxy]-tetrahydropyran as colorless oil (1:1 epimeric mixture).

g) 25.16 g (34.4 mmol) of (5S,7S)-2-[5,7-bis-(tert-butyl-diphenylsilanyloxy)-non-8-en-2-ynyloxy]-tetrahydro-pyran was deprotected by treatment at ambient temperature with 1.30 g (15 mol %) of pyridinium p-toluenesulfonate in 290 ml of abs. MeOH. The solution gradually became homogeneous. After 18 h the reaction mixture was quenched by pouring onto crushed ice/Na$_2$CO$_3$, extracted with ether, washed with water, dried over sodium sulfate and evaporated to dryness. Flash chromatography (SiO$_2$, hexane/AcOEt=82/18) yielded 19.17 g of (5S,7S)-5,7-bis-(tert-butyl-diphenyl-silanyloxy)-non-8-en-2-yn-1-ol as yellowish crystals of mp. 114–116°.

MS: (M-t-butyl)$^+$589.

h) 6.80 (10.5 mmol) of (5S,7S)-5,7-bis-(tert-butyl-diphenyl-silanyloxy)-non-8-en-2-yn-1-ol was dissolved in 40 ml of abs. EtOEt and treated at 0° with 8.0 ml of Red-Al (3.5M, toluene). After 90 minutes at RT, TLC indicated that some starting acetylene was still left. Additional 2 ml of Red-Al (3.5M, toluene) was added and allowed to react for further 2 h. While cooling with an ice bath, 1.13 ml of AcOEt was injected in order to destroy the excessive reagent. The reaction flask was then cooled down to −75° and treated with a solution of 8.95 g (35 mmol) of 12 in 45 ml of THF. After 15 minutes, the cooling bath was removed and the reaction mixture quenched when the internal temperature had reached −25°, by pouring onto crushed ice/sodium pyrosulfite. Extraction with ether, washing with water, drying over sodium sulfate and evaporation of solvents left a crude product, which was purified by flash chromatography (SiO$_2$, hexane/AcOEt=83/17) to yield 3.99 g of (Z)-(5R,7S)-5,7-bis-(tert-butyl-diphenyl-silanyloxy)-3-iodo-nona-2,8-dien-1-ol as a colorless gum.

MS (CI): (M+NH$_4$)$^+$792.

i) 3.99 g (5.15 mmol) of (Z)-(5R,7S)-5,7-bis-(tert-butyl-diphenyl-silanyloxy)-3-iodo-nona-2,8-dien-1-ol was dissolved in 34 ml of abs. CH$_3$CN and treated under careful exclusion of oxygen with 7.2 ml (10 eq.) of NEt$_3$ and 595 mg (515 μmol) of (Ph$_3$P)$_4$Pd. The mixture was kept at 60° for 5 h and then poured onto crushed ice/NH$_4$Cl, extracted with ether, washed with NH$_4$Cl, dried over sodium sulfate and evaporated to dryness. Flash chromatography (SiO$_2$, hexane/AcOEt=83/17) delivered 2.95 g of (Z)-(3S,5S)-2-[3,5-bis-(tert-butyl-diphenyl-silanyloxy)-2-methylene-cyclohexylidene]-ethanol as reddish foam.

MS: (M-H2O)$^+$628, (M-HOCH$_2$)$^+$615, (M-t-butyl)$^+$589.

j) 1.31 g (9.81 mmol) of N-chloro-succinimide in 34 ml of abs. CH$_2$Cl$_2$ was treated at −10° with 749 μl (10.2 mmol) of dimethyl sulfide. 15 Minutes later, 2.95 g (4.559 mmol) of (Z)-(3S,5S)-2-[3,5-bis-(tert-butyl-diphenyl-silanyloxy)-2-methylene-cyclohexylidene]-ethanol, dissolved in 10 ml of CH$_2$Cl$_2$, was slowly added to the resultant white suspension at the same temperature and then stirred for additional 30 minutes at RT. The reaction mixture was then poured onto crushed ice, extracted with ether, washed with water, dried over sodium sulfate and evaporated to dryness. Flash chromatography (SiO$_2$, hexane/AcOEt=97.5/2.5) yielded 2.76 g of (Z)-(3S,5S)-1-(2-chloro-ethylidene)-3,5-bis-(tert-butyl-diphenyl-silanyloxy)-2-methylene-cyclohexane as yellowish foam.

k) 847 μl (10.2 mmol) of diphenylphosphine in 16 ml of abs. THF was deprotonated at −10° with 3.05 ml nBuLi (1.5M, hexane). The solution was then cooled to −75° and 2.76 g (4.15 mmol) of (Z)-(3S,5S)-1-(2-chloro-ethylidene)-3,5-bis-(tert-butyl-diphenyl-silanyloxy)-2-methylene-cyclohexane, dissolved in 16 ml of abs. THF, was added dropwise. 10 Minutes later, 190 μl of water was injected and the reaction mixture allowed to reach room temperature. All solvents were then removed i.V., the residue taken up in 33 ml of CH$_2$Cl$_2$ and treated with 81 ml of 5% H$_2$O$_2$. After stirring for 75 minutes, the layers were separated, the queous phase extracted with AcOEt, the organic layers washed with sodium pyrosulfite, dried over sodium sulfate and evaporated to dryness. Flash chromatography (SiO$_2$, hexane/AcOEt=45/55) afforded 2.534 g of (Z)-(3S,5S)-[2 t-3,5-bis-(tert-butyl-diphenyl-silanyloxy)-2-methylene-cyclohexylidene]-ethyl]-diphenyl-phosphine oxide as colorless foam.

MS: (M)$^+$830, (M-t-butyl)$^+$773. NMR: (1H, δ, TMS) 0.94 (s, 9H), 1.04 (s, 9H), 1.96 (m, 1H), 2.11 (m, 1H), 2.89–3.05 (m, 2H), 3.11 (m, 1H), 3.36 (m, 1H), 4.73 (br s, 1H), 5.15 (q, 1H), 5.42 br s, 1H), 7.06 (dxt, 2H), 7.23–7.62 (m, 30 H).

The pharmacological properties of the compounds of the formula I can be determined by the following test procedures:

1. Calcium liability (tolerance test in mice):

This routine test gives a global picture of calcemic liability, indicating that compound s of this invention are well-tolerated and therefore have a low toxicity level. Profound changes in calcium homeostasis strongly affect the weight development of the animals. This parameter was used as a primary test for tolerance. Mice (25–30 g body weight) received daily subcutaneous (s.c.) administration of the vitamin D derivative for 4 consecutive days. Body weight was registered just before and at the end of a 5 day treatment period. The "highest tolerated dose" (HTD) in mice is the dose which results in zero weight gain during this treatment period.

For the well-known antipsoriatic compound 1,25-dihydroxycholecalciferol (calcitriol) an HTD s.c. of 0.5 μg/kg was obtained. For the compound of Example 1, the HTD s.c. was 10 μg/kg. For the compound of Example 2.3 the HTD s.c. was 0.9 μg/kg. For the compound of Example 2.4 the HTD s.c. was 400 μg/kg. For the compound of Example 2.8, the HTD s.c. was 1.5 μg/kg.

From the above results, it can be seen that the compounds of formula I are better tolerated than calcitriol.

2. Skin Effect

Orally administered vitamin D derivatives can lead to epidermal thickening (acanthosis) in hairless mice. This skin effect is considered as indicative for antipsoriatic potential of vitamin D analogues. The compounds were tested for 4 days at different dosages in order to detect analogues which show this epidermal effect at subtoxic and even non-toxic doses (dosage leading to slight or no weight loss). Calcitriol itself could not be dosed for 4 days at high enough levels to obtain this skin effect. The calcitriol data were obtained from animals treated for 2 days.

Hairless mice (Moro hr/hr) received daily administration of the test compounds in arachis oil by gavage for 4 days, using 2–5 different dosages (3 fold increments, 2 animals per dosage group). The mice were sacrificed at day 5 and skin biopsies taken, fixed in formalin and treated for histological evaluation. Daily measurements of body weight allowed to judge toxicity (calcium liability) and determine the non-toxic level defined as the dose which is tolerated without weight loss.

A score has been assigned to each analogue based on this skin effect (epidermal thickness of histological sections judged semi-quantitatively under the microscope) in relation to the tolerance (HTD), determined by weight change during the treatment period, as follows:

| Score | Epidermal Thickening at Tolerated Oral Dose |
|---|---|
| 0 | Inactive or Equal to Calcitriol |
| 1 | Moderate Effect, but Better than Calcitriol |
| 2 | Far Better than Calcitriol |

The results of the above tests are given in the following Table:

| Compound of Example | 1 | 2.3 | 2.4 | 2.8 | Calcitriol |
|---|---|---|---|---|---|
| HTD μg/kg | 10 | 0.9 | 400 | 1.5 | 0.5 |
| Skin effect score | 2 | 2 | 1 | 0 | 0 |

The compounds of formula I as described above can be administered orally, for the treatment of hyperproliferative skin diseases such as psoriasis, basal cell carcinomas, disorders of keratinization, and keratosis, or for the treatment of neoplastic diseases such as leukemia, or for the treatment of diseases which require modulation of the immune system, such as multiple sclerosis, transplant rejection, graft vs. host disease, or for the treatment of osteoporosis and hyperparathyroidism, to warmblooded animals which need such treatment. More specifically, the compounds of formula I as described above can be administered orally to an adult human in dosages that are in the range of about 0.5 to 1000 μg per day for the treatment of the above diseases.

The compounds of formula I as described above can be administered topically, for the treatment of hyperproliferative skin diseases such as psoriasis, to warmblooded animals which need such treatment. More specifically, the compounds of formula I as described above can be administered topically in dosages that are in the range of about 0.5 to 1000 μg per gram of topical formulation per day, for the treatment of the above diseases.

The dosage of the compounds of formula I can vary within wide limits depending on the illness to be treated, the age and the individual condition of the patient and on the mode of administration and will, of course, be fitted to the individual requirements in each particular case.

Oral dosage forms comprising compounds of formula I of the invention may be incorporated in capsules, tablets and the like with pharmaceutically acceptable carrier materials. Illustrative of such carrier materials which may be incorporated into capsules, and the like are the following: an emulsifier such as polyethylene glycol; a solubilizer such as a short chain triglyceride, e.g. Miglyol; a binder such as gum tragacanth, acacia, corn starch, or gelatin; an excipient such as dicalcium phosphate; a disintegrating agent such as corn starch, potato starch, algenic acid, and the like; a lubricant such as magnesium stearate, a sweetening agent such as sucrose, lactose, or saccharin; a flavoring agent such as peppermint, oil of wintergreen or cherry. Various other materials may be present as coating or to otherwise modify the physical form of the dosage unit. For instance, tablets may be coated with shellac, sugar, or both. A syrup or elixir may contain the active compound, sucrose as a sweetening agent, methyl and propyl parabens as preservatives, a dye, and a flavoring such as cherry or orange flavor.

Topical dosage forms comprising compounds of formula I of the invention include: ointments and creams encompassing formulations having oleaginous, absorbable, water-soluble and emulsion-type bases such as petrolatum, lanolin, polyethylene glycols and the like. Lotions are liquid preparations and vary from simple solutions to aqueous or hydroalcoholic preparations containing finely divided substances. Lotions can contain suspending or dispersing agents, for example, cellulose derivatives such as ethyl cellulose, methyl cellulose, and the like; gelatin or gums, which incorporate the active ingredient in a vehicle made up of water, alcohol, glycerin and the like. Gels are semi-solid preparations made by gelling a solution or suspension of the active ingredient in a carrier vehicle. The vehicles, which can be hydrous or anhydrous, are gelled using a gelling agent, such as, carboxy polymethylene, and neutralized to a proper gel consistency with the use of alkalies, such as, sodium hydroxide and amines, such as, polyethylenecocoamine.

As used herein, the term "topical" denotes the use of the active ingredient, incorporated in a suitable pharmaceutical carrier, and applied at the site of the disorder for the exertion of local action. Accordingly, the topical composition include those pharmaceutical forms in which the compound is applied externally by direct contact with the skin. The topical dosage forms comprise gels, creams, lotions, ointments, powders, aerosols and other conventional forms for applying medication to the skin obtained by admixing the compounds of formula I with known pharmaceutical topical carrier materials.

The following pharmaceutical compositions can be prepared in a manner known per se:

| Example A | | |
|---|---|---|
| Soft Gelatine Capsule | | mg/Capsule |
| Compound I | | 0.0001–1 |
| Butylated Hydroxytoluene (BHT) | | 0.016 |
| Butylated Hydroxyanisole (BHA) | | 0.016 |
| Fractionated Coconut Oil (Neobee M-5) or Miglyol 812 | q.s. | 160.0 |

| Example B | | |
|---|---|---|
| Soft Gelatine Capsule | | mg/Capsule |
| Compound I | | 0.0001–1 |
| α-Tocopherol | | 0.016 |
| Miglyol 812 | q.s. | 160.0 |

| Example C | |
|---|---|
| Topical Cream | mg/g |
| Compound I | 0.005–1 |
| Cetyl Alcohol | 1.5 |
| Stearyl Alcohol | 2.5 |
| Span 60 (Sorbitan monostearate) | 2.0 |
| Arlacel 165 (Glyceryl monostearate and polyoxyethylene glycol stearate blend) | 4.0 |
| Tween 60 (polysorbate 60) | 1.0 |
| Mineral Oil | 4.0 |
| Propylene Glycol | 5.0 |
| Propylparaben | 0.05 |
| BHA 0.05 | |
| Sorbitol Solution | 2.0 |
| Edetate Disodium | 0.01 |
| Methylparaben | 0.18 |
| Distilled Water | q.s. |

| Example D | |
|---|---|
| Topical ointment | mg/g |
| Compound I | 0.005–1 |
| Propylene glycol | exc. ad ung. pro 1 g |

We claim:
1. A compound of formula I:

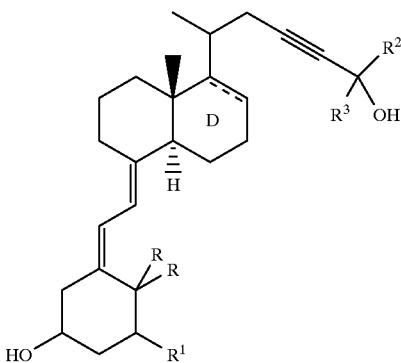

wherein the dotted carbon-carbon bond in the D-ring is C—C or C=C;
C(R,R) is CH$_2$ or C=CH$_2$,
R$^1$ is H, F or OH,
R$^2$ and R$^3$ are each independently C$_{1-4}$-alkyl or CF$_3$, or together with the carbon to which they are bound form C$_{3-6}$-cycloalkyl.

2. The compound of claim 1, wherein R$^2$ and R$^3$ are CF$_3$.

3. The compound of claim 1, wherein R$^2$ and R$^3$ are C$_{1-4}$-alkyl.

4. The compound of claim 1, wherein R$^2$ and R$^3$ together with the carbon to which they are bound form C$_{3-6}$-cycloalkyl.

5. A compound of claim 2 which is (5Z,7E)-(1S,3R)-1,26,26,26,27,27,27-heptafluoro-D-homo-9,10-secocholesta-5,7,10(19),17-tetraen-23-yne-3,25-diol.

6. A compound of claim 3 which is (5Z,7E)-(3S)-D-homo-9,10-secocholesta-5,7,10(19),17-tetraen-23-yne-3,25-diol.

7. A compound of claim 3 which is (7E)-(1R,3R,20S)-D-homo-19-nor-9,10-secocholesta-5,7,17-trien-23-yne-1,3,25-triol.

8. A compound of claim 3 which is (5Z,7E)-(3S,20S)-D-homo-9,10-secocholesta-5,7,10(19),17-tetraen-23-yne-3,25-diol.

9. A compound of claim 4 which is (7E)-(1R,3R)-24-(1-hydroxy-cyclohexyl)-D-homo-9,10-secochola-5,7,17-trien-23-yne-1,3-diol.

10. A compound of claim 2 which is (7E)-(1R,3R)-26,26,26,27,27,27-hexafluoro-D-homo-9,10-secocholesta-5,7,17-trien-23-yne-1,3,25-triol.

11. A compound of claim 3 which is (7E)-(1R,3R)-17a,26a,27a-trihomo-9,10-secocholesta-5,7,17-trien-23-yne-1,3,25-triol.

12. A compound of claim 4 which is (5Z,7E)-(1S,3R)-24-(1-hydroxy-cyclohexyl)-D-homo-9,10-secochola-5,7,10(19),17-tetraen-23-yne-1,3-diol.

13. A compound of claim 4 which is (5Z,7E)-(3S)-24-(1-hydroxy-cyclohexyl)-D-homo-9,10-secochola-5,7,10(19),17-tetraen-23-yne-3-ol.

14. A compound of claim 3 which is (5Z,7E)-(1S,3R)-17a,26a,27a-trihomo-9,10-secocholesta-5,7,10(19),17-tetraen-23-yne-1,3,25-triol.

15. A compound of claim 3 which is (5Z,7E)-(3S)-17a,26a,27a-trihomo-9,10-secocholesta-5,7,10(19),17-tetraen-23-yne-3,25-diol.

16. A compound of claim 4 which is (7E)-(1R,3R)-24-(1-hydroxy-cyclopentyl)-D-homo-9,10-secochola-5,7,17-trien-23-yne-1,3-diol.

17. A compound of claim 4 which is (5Z,7E)-(1S,3R)-24-(1-hydroxy-cyclopentyl)-D-homo-9,10-secochola-5,7,10(19),17-tetraen-23-yne-1,3-diol.

18. A compound of claim 3 which is (5Z,7E)-(1S,3S)-D-homo-9,10-secocholesta-5,7,10(19),17-tetraen-23-yne-3,25-diol.

19. A compound of claim 2 which is (5Z,7E)-(1S,3S)-26,26,26,27,27,27-hexafluoro-1-homo-9,10-secocholesta-5,7,10(19),17-tetraen-23-yne-1,3,25-triol.

20. A compound of claim 3 which is (5Z,7E)-(1S,3R)-1-fluoro-D-homo-9,10-secocholesta-5,7,10(19),17-tetraen-23-yne-3,25-diol.

21. A compound of claim 3 which is (7E)-(1R,3R)-D-homo-19-nor-9,10-secocholesta-5,7-dien-23-yne-1,3,25-triol.

22. A compound of claim 3 which is (5Z,7E)-(1R,3R)-D-homo-9,10-secocholesta-5,7,10(19)-trien-23-yne-1,3,25-triol.

23. A compound of claim 3 which is (5Z,7E)-(1S,3S)-D-homo-9,10-secocholesta-5,7,10(19)-trien-23-yne-1,3,25-triol.

24. A compound of claim 3 which is (5Z,7E)-(1S,3R)-D-homo-9,10-secocholesta-5,7,10(19)-trien-23-yne-1,3,25-triol.

25. A compound of claim 3 which is (5Z,7E)-(3S)-D-homo-9,10-seco-cholesta-5,7,10(19)-trien-23-yne-3,25-diol.

26. A compound of claim 4 which is (5Z,7E)-(3S)-24-(1-hydroxycyclopentyl)-D-homo-9,10-seco-chola-5,7,10(19),17-tetraen-23-yne-3-ol.

27. A compound of claim 2 wherein R$^1$ is OH and the dotted carbon-carbon bond on the D ring is C=C.

28. A compound of claim 3 wherein R1 is OH, R$^2$ and R$^3$ are CH$_3$ and the dotted carbon-carbon bond on the D ring is C=C.

29. A compound of claim 4 wherein R$^1$ is OH, and the dotted carbon-carbon bond on the D ring is C=C.

30. A compound of claim 27 which is (5Z,7E)-(1S,3R)-D-homo-9,10-secocholesta-5,7,10(19),17-tetraen-23-yne-1,3,25-triol.

31. A compound of claim 27 which is (7E)-(1R,3R)-D-homo-19-nor-9,10-secocholesta-5,7,17-trien-23-yne-1,3,25-triol.

32. A compound of claim 27 which is (5Z,7E)-(1S,3R,20S)-D-homo-9,10-secocholesta-5,7,10(19),17-tetraen-23-yne-1,3,25-triol.

33. A compound of formula II

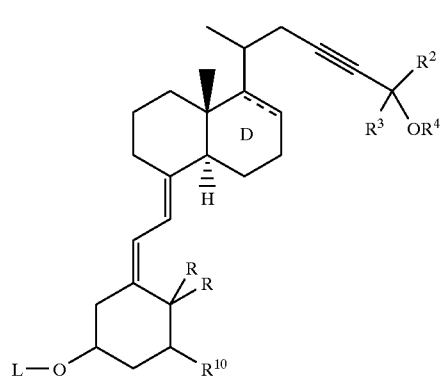

wherein the dotted bond is a C—C or C=C, C(R,R) is CH$_2$ or C=CH$_2$, and R$^2$ and R$^3$ are independently each C$_{1-4}$alkyl or CF$_3$, or together with the carbon to which they are bound form $C_{3-6}$-cycloalkyl $R^4$ is H or L', and $R^{10}$ is H, F or O-L, wherein L and L' are tert-butyl-dimethylsilyl, tert-butyl-diphenylsilyl or trimethylsilyl.

34. A compound of formula IV

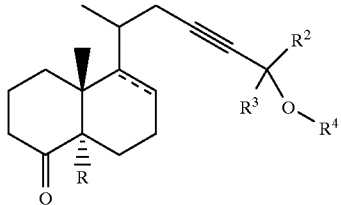

IV wherein the dotted bond is a C—C or C=C, C(R,R) is $CH_2$ or C=$CH_2$, and $R^2$ and $R^3$ are independently each $C_{1-4}$-alkyl or $CF_3$, or together with the carbon to which they are bound form $C_{3-6}$-cycloalkyl $R^4$ is H or L', and $R^{10}$ is H, F or O-L, wherein L and L' are tert-butyl-dimethylsilyl, tert-butyl-diphenylsilyl or trimethylsilyl.

35. A process for the manufacture of a compound of formula I which comprises cleaving the protecting groups in a compound of formula

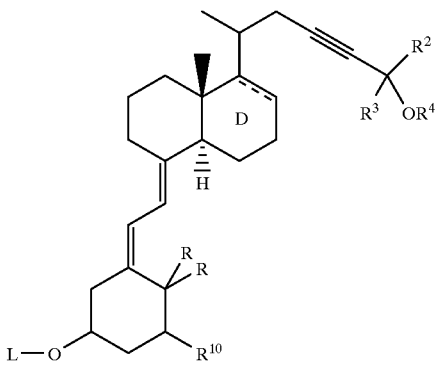

II wherein the dotted bond is a C—C or C=C, C(R,R) is $CH_2$ or C=$CH_2$, and $R^2$ and $R^3$ are independently each $C_{1-4}$-alkyl or $CF_3$, or together with the carbon to which they are bound form $C_{3-6}$-cycloalkyl $R^4$ is H or L', and $R^{10}$ is H, F or O-L, wherein L and L' are tert-butyl-dimethylsilyl, tert-butyl-diphenylsilyl or trimethylsilyl.

\* \* \* \* \*

UNITED STATES PATENT AND TRADEMARK OFFICE
CERTIFICATE OF CORRECTION

PATENT NO. : 5,919,986
DATED : July 6, 1999
INVENTOR(S) : Barbier, et al.

It is certified that error appears in the above-identified patent and that said Letters Patent is hereby corrected as shown below:

Claim 19, Column 26, line 8: "-1-homo" should read — -D-homo —.

Claim 34, Column 27, lines 5-15, Formula IV

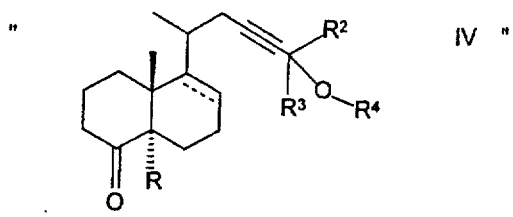

should read

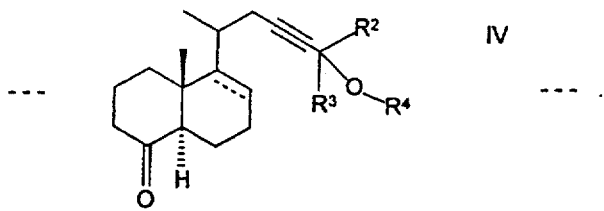

Signed and Sealed this

Thirtieth Day of November, 1999

*Attest:*

Q. TODD DICKINSON

*Attesting Officer*   Acting Commissioner of Patents and Trademarks